United States Patent
Prat Queralt et al.

(10) Patent No.: US 6,914,146 B2
(45) Date of Patent: Jul. 5, 2005

(54) METHODS OF USING ESTERQUATS HAVING ACYL GROUPS DERIVED FROM SHORT-CHAIN MONOCARBOXYLIC ACIDS AND SHORT-CHAIN DICARBOXYLIC ACIDS TO IMPROVE COSMETIC COMPOSITIONS

(75) Inventors: Esther Prat Queralt, Alella (ES); Cristina Amela Conesa, Cerdanyola del Valles (ES)

(73) Assignee: Cognis Iberia, S.L., Barcelona (ES)

(*) Notice: Subject to any disclaimer, the term of this patent is extended or adjusted under 35 U.S.C. 154(b) by 25 days.

(21) Appl. No.: 10/476,558
(22) PCT Filed: Apr. 20, 2002
(86) PCT No.: PCT/EP02/04372
§ 371 (c)(1),
(2), (4) Date: Oct. 30, 2003
(87) PCT Pub. No.: WO02/087535
PCT Pub. Date: Nov. 7, 2002

(65) Prior Publication Data
US 2004/0180028 A1 Sep. 16, 2004

(30) Foreign Application Priority Data
Apr. 30, 2001 (EP) .............................. 01110627

(51) Int. Cl.$^7$ ............................... C07C 101/00
(52) U.S. Cl. ........................... 554/110; 510/123
(58) Field of Search ..................... 554/110; 510/123

(56) References Cited

U.S. PATENT DOCUMENTS

| | | |
|---|---|---|
| 4,172,887 A | 10/1979 | Vanlerberghe et al. |
| 5,705,169 A | 1/1998 | Stein et al. |
| 5,718,891 A | 2/1998 | Prat et al. |
| 5,730,960 A | 3/1998 | Stein et al. |
| 5,869,716 A | 2/1999 | Pl Subirana et al. |
| 5,945,091 A | 8/1999 | Habeck et al. |
| 6,193,960 B1 | 2/2001 | Metzger et al. |
| 6,432,895 B1 * | 8/2002 | Bigorra et al. ............. 510/123 |

FOREIGN PATENT DOCUMENTS

| | | |
|---|---|---|
| DE | 1 165 574 A | 3/1964 |
| DE | 2 024 051 A | 12/1971 |
| DE | 43 08 794 C1 | 4/1994 |
| DE | 197 12 033 A1 | 9/1998 |
| DE | 197 43 687 C1 | 11/1998 |
| DE | 197 56 377 A1 | 5/1999 |
| DE | 199 61 939 A1 | 6/2001 |
| DE | 199 62 874 A1 | 6/2001 |
| DE | 100 19 142 A1 | 10/2001 |
| EP | 0 693 471 B1 | 1/1996 |
| EP | 0 694 521 B1 | 1/1996 |
| EP | 0 750 606 B1 | 1/1997 |
| EP | 0 818 450 B1 | 1/1998 |
| FR | 2 252 840 A | 9/1975 |
| GB | 962 919 A | 7/1964 |
| GB | 1 333 475 A | 10/1973 |
| WO | WO 91/01295 | 2/1991 |

OTHER PUBLICATIONS

Puchta, et al., "A New Generation of Softeners", Tenside Surf. Det., vol. 30, Carl Hanser Verlag, München, (1993), pp. 186–191.

R. Lagerman, et al., "Synthesis and Performance of Ester Quatrnary Biodegradable Softeners", JAOCS, vol. 71, No. 1, (Jan., 1994), pp. 97–99.

Shapiro, et al., "Environmentally Friendly Ester Quats", Cosmetics & Toiletries, vol. 109, Allured Publishing Corp., (Dec., 1994), pp. 77–78 & 80.

Falbe, "Surfactants in Consumer Products", Springer Verlag, Berlin, (1987), pp. 54–124.

R. Lochhead et al., "Encyclopedia of Polymers and Thickeners for Cosmetics", Cosmetics & Toiletries, vol. 108, (May, 1993), pp. 95–114, 116–124, 127–130, 132–135.

C. Todd et al., "Volatile silicone fluids for cosmetic formulations", Cosmetics and Toiletries, vol. 91, (Jan., 1976), pp. 29–32.

* cited by examiner

Primary Examiner—Deborah D Carr
(74) Attorney, Agent, or Firm—Aaron R. Ettelman

(57) ABSTRACT

Methods of improving the stability of a composition containing a long-chain esterquat and methods of improving the microbicidal properties of a cosmetic composition are described wherein a short-chain esterquat having acyl groups derived from a mixture of at least one monocarboxylic acid having from 6 to 10 carbon atoms, and at least one dicarboxylic acid having from 2 to 12 carbon atoms is combined with a cosmetic composition.

20 Claims, No Drawings

METHODS OF USING ESTERQUATS HAVING ACYL GROUPS DERIVED FROM SHORT-CHAIN MONOCARBOXYLIC ACIDS AND SHORT-CHAIN DICARBOXYLIC ACIDS TO IMPROVE COSMETIC COMPOSITIONS

BACKGROUND OF THE INVENTION

Manufacturers of cosmetic products are not only interested in continually improving the properties of their products and in meeting growing consumer demands, they are also—conversely—seeking to keep the number of raw materials used as small as possible in order to arrest increasing raw material costs by eliminating complexity. For this reason, there is a particular demand for raw materials which not only have improved properties, but also show additional effects such as, for example, stabilization (for example in the case of active substances) or the replacement of other formulation ingredients (for example preservatives).

In recent years, cationic surfactants of the esterquat type have grown into important cosmetic raw materials because they not only have good dermatological compatibility, they also condition the skin and the hair, i.e. provide them with pleasant sensory properties, more especially a particular softness. The esterquats used for this purpose are quaternized esters of alkanolamines with long-chain fatty acids ($C_{12-20}$ range) which, unfortunately, sometimes show two disadvantages in the end formulations, i.e. separation of the emulsions or gelation are observed in the event of prolonged storage, particularly under temperature stress, which are both undesirable to the consumer.

Accordingly, the complex problem addressed by the present invention was to find a way of enabling relatively long-chain esterquats to be more easily and stably incorporated in cosmetic preparations while, at the same time, saving preservative and also improving the stability of special active ingredients, such as UV filters for example.

BRIEF SUMMARY OF THE INVENTION

The present invention relates, in general, to the field of cosmetology and, more particularly, to the use of special cationic surfactants for the production of corresponding preparations.

(a) monocarboxylic acids containing 6 to 10 carbon atoms and (b) dicarboxylic acids containing 2 to 12 carbon atoms.

It has surprisingly been found that esterquats of which the acyl component derives from short-chain fatty acids in combination with dicarboxylic acids facilitate the incorporation of relatively long-chain esterquats. In particular, storage and thermal stability are improved and the unwanted effect of gelation is counteracted. At the same time, the esterquats to be used in accordance with the invention have microbicidal properties so that far less preservative has to be used to stop the cosmetic preparations from spoiling. In some cases, there is no need whatever to add preservatives. Finally, it was found that photolabile active substances, such as UV filters or retinol for example, are more slowly degraded in the presence of the special esterquats.

DETAILED DESCRIPTION OF THE INVENTION

"Esterquats" are generally understood to be quaternized fatty acid triethanolamine ester salts. These are known compounds which can be obtained by the relevant methods of preparative organic chemistry. Reference is made in this connection to International patent application WO 91/01295 (Henkel), according to which triethanolamine is partly esterified with fatty acids in the presence of hypophosphorous acid, air is passed through the reaction mixture and the whole is then quaternized with dimethyl sulfate or ethylene oxide. In addition, German patent DE 4308794 C1 (Henkel) describes a process for the production of solid esterquats in which the quaternization of triethanolamine esters is carried out in the presence of suitable dispersants, preferably fatty alcohols. Overviews on this theme have been published by R. Puchta et al. in Tens. Surf. Det., 30, 186 (1993), by M. Brock in Tens. Surf. Det., 30, 394 (1993), by R. Lagerman et al. in J. Am. Oil Chem. Soc., 71, 97 (1994) and by I. Shapiro in Cosm. Toil. 109, 77 (1994).

Typical examples of esterquats suitable for use in accordance with the invention are products of which the acyl component (a) derives from monocarboxylic acids corresponding to formula (I):

$$R^1CO\text{—}OH \qquad (I)$$

in which $R^1CO$ is an acyl group containing 6 to 10 carbon atoms. Examples of such monocarboxylic acids are caproic acid, caprylic acid, capric acid and technical mixtures thereof such as, for example, so-called head-fractionated fatty acid. Esterquats of which the acyl component (a) derives from monocarboxylic acids of formula (I), in which $R^1CO$ is a linear, saturated acyl group containing 8 to 10 carbon atoms, are preferably used.

Other esterquats used in accordance with the invention are those of which the acyl component (b) derives from dicarboxylic acids corresponding to formula (II):

$$HOOC(CH_2)_nCOOH \qquad (II)$$

in which n is a number of 1 to 10. Examples of such dicarboxylic acids are malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component (a) derives from monocarboxylic acids corresponding to formula (I), where $R^1CO$ is a linear saturated acyl group containing 6 to 22 carbon atoms, and of which the acyl component (b) derives from adipic acid are preferably used. The molar ratio of component (a) to component (b) may be in the range from 1:99 to 99:1 and is preferably in the range from 50:50 to 90:10 and more particularly in the range from 70:30 to 80:20.

A special embodiment of the invention is characterized by the use of esterquats which represent quaternized fatty acid triethanolamine ester salts corresponding to formula (III):

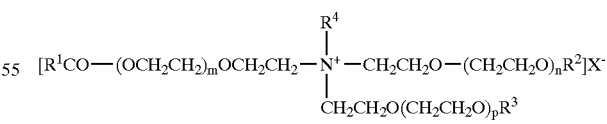

$$[R^1CO\text{—}(OCH_2CH_2)_mOCH_2CH_2\text{—}\overset{R^4}{\underset{CH_2CH_2O(CH_2CH_2O)_pR^3}{N^+}}\text{—}CH_2CH_2O\text{—}(CH_2CH_2O)_nR^2]X^- \qquad (III)$$

in which $R^1CO$ stands for mixtures of mono- and dicarboxylic acids, $R^2$ and $R^3$ independently of one another represent hydrogen or have the same meaning as $R^1CO$, $R^4$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate.

Besides the quaternized fatty acid triethanolamine ester salts, other suitable esterquats are quaternized ester salts of mono-/dicarboxylic acid mixtures with diethanolalkyamines corresponding to formula (IV):

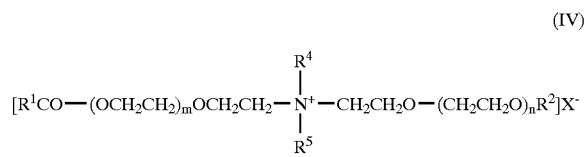

in which $R^1CO$ represents mixtures of mono- and dicarboxylic acids, $R^2$ is hydrogen or has the same meaning as $R^1CO$, $R^4$ and $R^5$ independently of one another are alkyl groups containing 1 to 4 carbon atoms, m and n together stand for 0 or numbers of 1 to 12 and X stands for halide, alkyl sulfate or alkyl phosphate.

Another group of suitable esterquats are the quaternized ester salts of mono-/dicarboxylic acid mixtures with 1,2-dihydroxypropyl dialkylamines corresponding to formula (V):

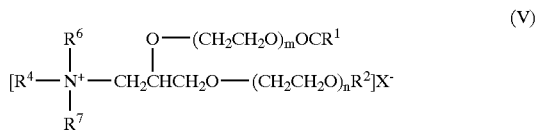

in which $R^1CO$ represents mixtures of mono- and dicarboxylic acids, $R^2$ is hydrogen or has the same meaning as $R^1CO$, $R^4$, $R^6$ and $R^7$ independently of one another are alkyl groups containing 1 to 4 carbon atoms, m and n together stand for 0 or numbers of 1 to 12 and X stands for halide, alkyl sulfate or alkyl phosphate.

In addition, other suitable esterquats are substances in which the ester bond is replaced by an amide bond and which—preferably based on diethylenetriamine—correspond to formula (VI):

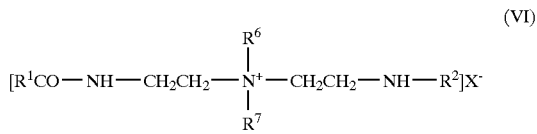

in which $R^1CO$ represents mixtures of mono- and dicarboxylic acids, $R^2$ is hydrogen or has the same meaning as $R^1CO$, $R^6$ and $R^7$ independently of one another are alkyl groups containing 1 to 4 carbon atoms and X is halide, alkyl sulfate or alkyl phosphate. Amide esterquats such as these are commercially obtainable, for example, under the name of Incroquat® (Croda).

Finally, other suitable esterquats are compounds based on ethoxylated castor oil or hydrogenation products thereof which preferably correspond to formula (VII):

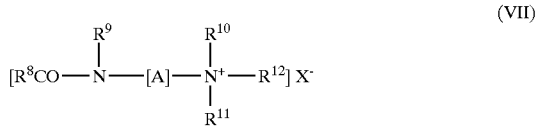

in which $R^8CO$ represents mixtures of mono- and dicarboxylic acids, A is a linear or branched alkylene group containing 1 to 6 carbon atoms, $R^9$, $R^{10}$ and $R^{11}$ independently of one another represent hydrogen or a $C_{1-4}$ alkyl group, $R^{12}$ is a $C_{1-4}$ alkyl group or a benzyl group and X is halogen, alkyl sulfate or alkyl phosphate.

So far as the choice of the preferred fatty acids and the optimal degree of esterification are concerned, the examples mentioned for (III) also apply to the esterquats corresponding to formulae (IV) to (VII).

The esterquats corresponding to formulae (III) to (VII) may be obtained both from fatty acids and from the corresponding triglycerides in admixture with the corresponding dicarboxylic acids. One such process, which is intended to be representative of the relevant prior art, is proposed in European patent EP 0750606 B1 (Cognis).

To produce the quaternized esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous.

The preferred esterquats are technical mixtures of mono-, di- and triesters with an average degree of esterification of 1.5 to 1.9.

Commercial Applications

The special esterquats are used for the production of cosmetic preparations in which they may be present in quantities of 0.1 to 10, preferably 1 to 8 and more particularly 2 to 5% by weight, based on the preparations. These preparations are preferably skin or hair treatment preparations which may also contain other auxiliaries and additives typical of such preparations. These include, for example, mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorizers, antiperspirants, antidandruff agents, film formers, swelling agents, insect repellents, self-tanning agents, tyrosine inhibitors (depigmenting agents), hydrotropes, solubilizers, preservatives, perfume oils, dyes and the like.

Surfactants

Suitable surfactants are anionic, nonionic, cationic and/or amphoteric or zwitterionic surfactants which are normally present in the preparations in quantities of about 1 to 70, preferably 5 to 50 and more particularly 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether)phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en) yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds such as, for example, dimethyl distearyl ammonium chloride and other esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols, silicone oils (Cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, $C_{12-22}$ fatty acids, alkyl phenols containing 8 to 15 carbon atoms in the alkyl group and alkylamines containing 8 to 22 carbon atoms in the alkyl group;

alkyl and/or alkenyl oligoglycosides containing 8 to 22 carbon atoms in the alk(en)yl group and ethoxylated analogs thereof;

adducts of 1 to 15 mol ethylene oxide with castor oil and/or hydrogenated castor oil;

adducts of 15 to 60 mol ethylene oxide with castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol ethylene oxide;

partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethylene glycol-30 Dipolyhydroxystearate;

polymer emulsifiers, for example Pemulen types (TR-1, TR-2) of Goodrich;

polyalkylene glycols and glycerol carbonate.

Ethylene Oxide Addition Products

The addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as lipid layer enhancers for cosmetic formulations from DE 20 24 051 PS.

Alkyl and/or Alkenyl Oligoglycosides

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, coco-fatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of *Cocamidopropyl Betaine* is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Finally, other suitable emulsifiers are cationic surfactants, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryidimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl4'-methoxydibenzoyl methane (Parsol 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to $\mu$mol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether(triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1, 2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blooms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:

astringent active principles, oil components, nonionic emulsifiers, co-emulsifiers, consistency factors, auxiliaries in the form of, for example, thickeners or complexing agents and/or non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils, synthetic skin-protecting agents and/or oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl)r-2-(1H-imidazol-1-ylmethyl)-1,3-dioxylan-c-4-ylmethoxy-phenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-Tanning Agents and Depigmentinq Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular preparations. The preparations may be produced by standard hot or cold processes and are preferably produced by the phase inversion temperature method.

EXAMPLES

Production Example 1

406 g (2.82 mol) caprylic acid, 206 g (1.41 mol) adipic acid and 0.8 g sodium hypophosphite were introduced into a 2-liter three-necked flask equipped with a stirrer, distillation head and vacuum connection and heated to 70° C. The pressure was then reduced to 35 mbar and 420 g (2.82 mol) triethanolamine were added in portions. The temperature was increased in steps to 165° C. and the pressure was reduced to 5 mbar until the separation of water stopped and the acid value had fallen to a value below 5 mg KOH/g. 871 g (2.72 mol) of the ester thus produced were transferred to a second flask and dissolved at 50° C. in 211 g isopropyl alcohol. 324 g (2.57 mol) dimethyl sulfate were then added in portions with stirring, the temperature being kept at 70° C. for 4 hours.

Production Example 2

424 g (2.73 mol) of a technical 1:1 mixture of caprylic and capric acid, 200 g (1.37 mol) adipic acid, 0.7 g sodium hypophosphite and 408 g (2.74 mol) triethanolamine were reacted as in Example 1. 871 g (2.63 mol) of the resulting ester were then dissolved in 132 g isopropyl alcohol and quaternized with 315 g (2.5 mol) dimethyl sulfate.

Production Example 3

292 g (1.70 mol) capric acid, 124 g (0.85 mol) adipic acid, 0.5 g sodium hypophosphite and 253 g (1.70 mol) triethanolamine were reacted as in Example 1. 582 g (1.63 mol) of the resulting ester were then dissolved in 137 g isopropyl alcohol and quaternized with 194 g (1.54 mol) dimethyl sulfate.

A number of Formulation Examples are shown in Table 1.

TABLE 1

Examples of cosmetic preparations (water, preservative to 100% by weight)

| Composition(INCI) | 1 | 2 | 3 | 4 | 5 | 6 | 7 | 8 | 9 | 10 |
|---|---|---|---|---|---|---|---|---|---|---|
| Texapon ® NSO<br>Sodium Laureth Sulfate | — | — | — | — | — | — | 38.0 | 38.0 | 25.0 | — |
| Texapon ® SB 3<br>Disodium Laureth Sulfosuccinate | — | — | — | — | — | — | — | — | 10.0 | — |
| Plantacare ® 818<br>Coco Glucosides | — | — | — | — | — | — | 7.0 | 7.0 | 6.0 | — |
| Plantacare ® PS 10<br>Sodium Laureth Sulfate (and) Coco Glucosides | — | — | — | — | — | — | — | — | — | 16.0 |
| Dehyton ® PK 45<br>Cocamidopropyl Betaine | — | — | — | — | — | — | — | — | 10.0 | — |
| Dehyquart ® A<br>Cetrimonium Chloride | 2.0 | 2.0 | 2.0 | 2.0 | 4.0 | 4.0 | — | — | — | — |
| Dehyquart L ® 80<br>Dococcoylmethylethoxymonium Methosulfate (and) Propyleneglycol | 1.2 | 1.2 | 1.2 | 1.2 | 0.6 | 0.6 | — | — | — | — |
| Dehyquart ® ABIO-8<br>Capryloyl/Adipinoyl Methylethoxymonium Methodsulfate | 1.0 | 1.0 | 1.0 | 1.0 | 1.0 | 1.0 | 1.0 | 1.0 | 1.0 | 1.0 |
| Eumulgin ® B2<br>Ceteareth-20 | 0.8 | 0.8 | — | 0.8 | — | 1.0 | — | — | — | — |
| Eumulgin ® VL 75<br>Lauryl Glucoside (and) Polyglyceryl-2 Polyhydroxystearate (and) Glycerin | — | — | 0.8 | — | 0.8 | — | — | — | — | — |
| Lanette ® O<br>Cetearyl Alcohol | 2.5 | 2.5 | 2.5 | 2.5 | 3.0 | 2.5 | — | — | — | — |
| Cutina ® GMS<br>Glyceryl Stearate | 0.5 | 0.5 | 0.5 | 0.5 | 0.5 | 1.0 | — | — | — | — |
| Cetiol ® HE<br>PEG-7 Glyceryl Cocoate | 1.0 | — | — | — | — | — | — | — | 1.0 | — |
| Cetiol ® PGL<br>Hexyldecanol (and) Hexyldecyl laurate | — | 1.0 | — | — | 1.0 | — | — | — | — | — |
| Cetiol ® V<br>Decyl Oleate | — | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soya Sterol | — | — | — | — | 1.0 | 1.0 | — | — | — | — |
| Hydagen ® CMF | 1.0 | 1.0 | 1.0 | 1.0 | 1.0 | 1.0 | 1.0 | 1.0 | 1.0 | 1.0 |

TABLE 1-continued

| Examples of cosmetic preparations (water, preservative to 100% by weight) | | | | | | | | | | |
|---|---|---|---|---|---|---|---|---|---|---|
| Chitosan | | | | | | | | | | |
| Copherol ® 1250<br>Tocopherol Acetate | — | — | 0.1 | 0.1 | — | — | — | — | — | — |
| Arlypon ® F<br>Laureth-2 | — | — | — | — | — | — | 3.0 | 3.0 | 1.0 | — |
| Sodium Chloride | — | — | — | — | — | — | — | 1.5 | — | 1.5 |
| Composition (INCI) | 11 | 12 | 13 | 14 | 15 | 16 | 17 | 18 | 19 | 20 |
| Texapon ® NSO<br>Sodium Laureth Sulfate | 20.0 | 20.0 | 12.4 | — | 25.0 | 11.0 | — | — | — | — |
| Texpon ® K 14 S<br>Sodium Myreth Sulfate | — | — | — | — | — | — | — | — | 11.0 | 23.0 |
| Texapon ® SB 3<br>Disodium Laureth Sulfosuccinate | — | — | — | — | — | 7.0 | — | — | — | — |
| Plantacare ® 818<br>Coco Glucosides | 5.0 | 5.0 | 4.0 | — | — | — | — | — | 6.0 | 4.0 |
| Plantacare ® 2000<br>Decyl Glucoside | — | — | — | — | 5.0 | 4.0 | — | — | — | — |
| Plantacare ® PS 10<br>Sodium Laureth Sulfate (and) Coco Glucosides | — | — | — | 40.0 | — | — | 16.0 | 17.0 | — | — |
| Dehyton ® PK 45<br>Cocamidopropyl Betaine | 20.0 | 20.0 | — | — | 8.0 | — | — | — | — | 7.0 |
| Dehyquart ® ABIO-8<br>Capryloyl/Adipinoyl Methylethoxymonium Methodsulfate | 1.0 | 1.0 | 1.0 | 1.0 | 1.0 | 1.0 | 1.0 | 1.0 | 1.0 | 1.0 |
| Eumulgin ® B1<br>Ceteareth-12 | — | — | — | — | 1.0 | — | — | — | — | — |
| Eumulgin ® B2<br>Ceteareth-20 | — | — | — | 1.0 | — | — | — | — | — | — |
| Lameform ® TGI<br>Polyglyceryl-3 Isostearate | — | — | — | 4.0 | — | — | — | — | — | — |
| Dehymuls ® PGPH<br>Polyglyceryl-2 Dipolyhydroxystearate | — | — | 1.0 | — | — | — | — | — | — | — |
| Monomuls ® 90-L 12<br>Glyceryl Laurate | — | — | — | — | — | — | — | — | 1.0 | 1.0 |
| Cetiol ® HE<br>PEG-7 Glyceryl Cocoate | — | 0.2 | — | — | — | — | — | — | — | — |
| Eutanol ® G<br>Octyldodecanol | — | — | — | 3.0 | — | — | — | — | — | — |
| Nutrilan ® Keratin W<br>Hydrolyzed Keratin | — | — | — | — | — | — | — | — | 2.0 | 2.0 |
| Nutrilan ® I<br>Hydrolyzed Collagen | 1.0 | — | — | — | 2.0 | — | 2.0 | — | — | — |
| Lamesoft ® LMG<br>Glyceryl Laurate (and) Potassium Cocoyl Hydrolyzed Collagen | — | — | — | — | — | — | — | — | 1.0 | — |
| Lamesoft ® 156<br>Hydrogenated Tallow Glyceride (and) Potassium Cocoyl Hyrolyzed Collagen | — | — | — | — | — | — | — | — | — | 5.0 |
| Gluadin ® WK<br>Sodium Cocoyl Hydrolyzed Wheat Protein | 1.0 | 1.5 | 4.0 | 1.0 | 3.0 | 1.0 | 2.0 | 2.0 | 2.0 | — |
| Euperlan ® PK 3000 AM<br>Glycol Distearate (and) Laureth-4 (and) Cocamidopropyl Betaine | 5.0 | 3.0 | 4.0 | — | — | — | — | 3.0 | 3.0 | — |
| Arlypon ® F<br>Laureth-2 | 2.6 | 1.6 | — | 1.0 | 1.5 | — | — | — | — | — |
| Hydagen ® CMF<br>Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |
| Glycerin (86% by weight) | — | 5.0 | — | — | — | — | — | 1.0 | 3.0 | — |
| Composition (INCI) | 21 | 22 | 23 | 24 | 25 | 26 | 27 | 28 | 29 | 30 |
| Texapon ® NSO<br>Sodium Laureth Sulfate | — | 30.0 | 30.0 | — | 25.0 | — | — | — | — | — |
| Plantacare ® 818<br>Coco Glucosides | — | 10.0 | — | — | 20.0 | — | — | — | — | — |
| Plantacare ® PS 10<br>Sodium Laureth Sulfate (and) Coco Glucosides | 22.0 | — | 5.0 | 22.0 | — | — | — | — | — | — |
| Dehyton ® PK 45<br>Cocamidopropyl Betaine | 15.0 | 10.0 | 15.0 | 15.0 | 20.0 | — | — | — | — | — |
| Dehyquart ® ABIO-8<br>Capryloyl/Adipinoyl Methylethoxymonium Methodsulfate | 1.0 | 1.0 | 1.0 | 1.0 | 1.0 | 1.0 | 1.0 | 1.0 | 1.0 | 1.0 |
| Emulgade ® SE<br>Glyceryl Stearate (and) Ceteareth 12/20 | — | — | — | — | — | 5.0 | 5.0 | 4.0 | — | — |

TABLE 1-continued

Examples of cosmetic preparations (water, preservative to 100% by weight)

| Composition (INCI) | | | | | | | | | | |
|---|---|---|---|---|---|---|---|---|---|---|
| (and) Cetearyl Alcohol (and) Cetyl Palmitate | | | | | | | | | | |
| Eumulgin ® B1 Ceteareth-12 | — | — | — | — | — | — | — | 1.0 | — | — |
| Lameform ® TGI Polyglyceryl-3 Isostearate | — | — | — | — | — | — | — | — | 4.0 | — |
| Dehymuls ® PGPH Polyglyceryl-2 Dipolyhydroxystearate | — | — | — | — | — | — | — | — | — | 4.0 |
| Monomuls ® 90-O 18 Glyceryl Oleate | — | — | — | — | — | — | — | — | 2.0 | — |
| Cetiol ® HE PEG-7 Glyceryl Cocoate | 2.0 | — | — | 2.0 | 5.0 | — | — | — | — | 2.0 |
| Cetiol ® OE Dicaprylyl Ether | — | — | — | — | — | — | — | — | 5.0 | 6.0 |
| Cetiol ® PGL Hexyldecanol (and) Hexyldecyl Laurate | — | — | — | — | — | — | — | 3.0 | 10.0 | 9.0 |
| Cetiol ® SN Cetearyl Isononanoate | — | — | — | — | — | 3.0 | 3.0 | — | — | — |
| Cetiol ® V Decyl Oleate | — | — | — | — | — | 3.0 | 3.0 | — | — | — |
| Myritol ® 318 Coco Caprylate Caprate | — | — | — | — | — | — | — | 3.0 | 5.0 | 5.0 |
| Bees Wax | — | — | — | — | — | — | — | — | 7.0 | 5.0 |
| Nutrilan ® Elastin E20 Hydrolyzed Elastin | — | — | — | — | — | 2.0 | — | — | — | — |
| Nutrilan ® I-50 Hydrolyzed Collagen | — | — | — | — | 2.0 | — | 2.0 | — | — | — |
| Gluadin ® AGP Hydrolyzed Wheat Gluten | 0.5 | 0.5 | 0.5 | — | — | — | — | 0.5 | — | — |
| Gluadin ® WK Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM Glycol Distearate (and) Laureth-4 (and) Cocamidopropyl Betaine | 5.0 | — | — | 5.0 | — | — | — | — | — | — |
| Arlypon ® F Laureth-2 | — | — | — | — | — | — | — | — | — | — |
| Hydagen ® CMF Chitosan | 1.0 | 1.0 | 1.0 | 1.0 | 1.0 | 1.0 | 1.0 | 1.0 | 1.0 | 1.0 |
| Magnesium Sulfate Hepta Hydrate | — | — | — | — | — | — | — | — | 1.0 | 1.0 |
| Glycerin (85% by weight) | — | — | — | — | — | 3.0 | 3.0 | 5.0 | 5.0 | 3.0 |

| Composition (INCI) | 31 | 32 | 33 | 34 | 35 | 36 | 37 | 38 | 39 | 40 |
|---|---|---|---|---|---|---|---|---|---|---|
| Dehymuls ® PGPH Polyglyceryl-2 Dipolyhydroxystearate | 4.0 | 3.0 | — | 5.0 | — | — | — | — | — | — |
| Lameform ® TGI Polyglyceryl-3 Diisostearate | 2.0 | 1.0 | — | — | — | — | — | — | — | — |
| Emulgade ® PL 68/50 Cetearyl Glucoside (and) Cetearyl Alcohol | — | — | — | — | 4.0 | — | — | — | 3.0 | — |
| Eumulgin ® B2 Ceteareth-20 | — | — | — | — | — | — | — | 2.0 | — | — |
| Tegocare ® PS Polyglyceryl-3 Methylglucose Distearate | — | — | 3.0 | — | — | — | 4.0 | — | — | — |
| Eumulgin VL 75 Polyglyceryl-2 Dipolyhydroxystearate (and) Lauryl Glucoside (and) Glycerin | — | — | — | — | — | 3.5 | — | — | 2.5 | — |
| Dehyquart ® ABIO-8 Capryloyl/Adipinoyl Methylethoxymonium Methodsulfate | 1.0 | 1.0 | 1.0 | 1.0 | 1.0 | 1.0 | 1.0 | 1.0 | 1.0 | 1.0 |
| Bees Wax | 3.0 | 2.0 | 5.0 | 2.0 | — | — | — | — | — | — |
| Cutina ® GMS Glyceryl Stearate | — | — | — | — | — | 2.0 | 4.0 | — | — | 4.0 |
| Lanette ® O Cetearyl Alcohol | — | — | 2.0 | — | 2.0 | 4.0 | 2.0 | 4.0 | 4.0 | 1.0 |
| Antaron ® V 216 PVP/Hexadecene Copolymer | — | — | — | — | 3.0 | — | — | — | — | 2.0 |
| Myritol ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Cetiol ® J 600 Oleyl Erucate | 7.0 | 4.0 | 3.0 | 5.0 | 4.0 | 3.0 | 3.0 | — | 5.0 | 4.0 |
| Cetiol ® OE Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |

TABLE 1-continued

| Examples of cosmetic preparations (water, preservative to 100% by weight) | | | | | | | | | | |
|---|---|---|---|---|---|---|---|---|---|---|
| Hydagen ® CMF Chitosan | 1.0 | 1.0 | 1.0 | 1.0 | 1.0 | 1.0 | 1.0 | 1.0 | 1.0 | 1.0 |
| Copherol ® F 1300 Tocopherol/Tocopheryl Acetate | 0.5 | 1.0 | 1.0 | 2.0 | 1.0 | 1.0 | 1.0 | 2.0 | 0.5 | 2.0 |
| Neo Heliopan ® Hydro Sodium Phenylbenzimidazole Sulfonate | 3.0 | — | — | 3.0 | — | — | 2.0 | — | 2.0 | — |
| Neo Heliopan ® 303 Octocrylene | — | 5.0 | — | — | — | 4.0 | 5.0 | — | — | 10.0 |
| Neo Heliopan ® BB Benzophenone-3 | 1.5 | — | — | 2.0 | 1.5 | — | — | — | 2.0 | — |
| Neo Heliopan ® E 1000 Isoamyl p-Methoxycinnamate | 5.0 | — | 4.0 | — | 2.0 | 2.0 | 4.0 | 10.0 | — | — |
| Neo Heliopan ® AV Octyl Methoxycinnamate | 4.0 | — | 4.0 | 3.0 | 2.0 | 3.0 | 4.0 | — | 10.0 | 2.0 |
| Uvinul ® T 150 Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerol (86% by weight) | 5.0 | 5.0 | 5.0 | 5.0 | 5.0 | 5.0 | 5.0 | 5.0 | 5.0 | 5.0 |

(1–4) Hair rinse,
(5–6) Conditioner,
(7–8) Shower bath,
(9) Shower gel,
(10) Wash lotion
(11–14) "Two-in-one" shower bath,
(15–20) Shampoo
(21–25) Foam bath,
(26) Soft cream,
(27, 28) Moisturising emulsion,
(29, 30) Night cream
(31) W/O sun protection cream,
(32–34) W/O sun protection lotion,
(35, 38, 40) O/W sun protection lotion,
(36, 27, 39) 0/W sun protection cream

What is claimed is:

1. A method of improving the stability of a composition containing a long-chain esterquat, said method comprising:
   (a) providing a composition containing a long-chain esterquat;
   (b) providing a short-chain esterquat having acyl groups derived from a mixture of at least one monocarboxylic acid having from 6 to 10 carbon atoms, and at least one dicarboxylic acid having from 2 to 12 carbon atoms; and
   (c) combining the composition and the short-chain esterquat.

2. The method according to claim 1, wherein the at least one monocarboxylic acid comprises an acid corresponding to the general formula (I):

$$R^1CO\text{—}OH \quad (I)$$

wherein $R^1CO$ represents an acyl group having from 6 to 10 carbon atoms.

3. The method according to claim 2, wherein $R^1CO$ represents a linear, saturated acyl group having from 8 to 10 carbons atoms.

4. The method according to claim 1, wherein the at least one dicarboxylic acid comprises an acid corresponding to the general formula (II):

$$HOOC(CH_2)_nCOOH \quad (II)$$

wherein n represents a number of from 1 to 10.

5. The method according to claim 1, wherein the at least one dicarboxylic acid comprises adipic acid.

6. The method according to claim 3, wherein the at least one dicarboxylic acid comprises adipic acid.

7. The method according to claim 1, wherein the acyl groups derived from the at least one monocarboxylic acid and the acyl groups derived from the at least one dicarboxylic acid are present in a molar ratio of from 50:50 to 90:10.

8. The method according to claim 1, wherein the acyl groups derived from the at least one monocarboxylic acid and the acyl groups derived from the at least one dicarboxylic acid are present in a molar ratio of from 70:30 to 80:20.

9. The method according to claim 1, wherein the short-chain esterquat is combined with the composition in an amount of from 0.1 to 10% by weight, based on the composition.

10. The method according to claim 1, wherein the short-chain esterquat is combined with the composition in an amount of from 1 to 8% by weight, based on the composition.

11. A method of improving the microbicidal properties of a cosmetic composition, said method comprising:
   (a) providing a cosmetic composition containing at least one component subject to microbial spoiling;
   (b) providing a short-chain esterquat having acyl groups derived from a mixture of at least one monocarboxylic acid having from 6 to 10 carbon atoms, and at least one dicarboxylic acid having from 2 to 12 carbon atoms; and
   (c) combining the cosmetic composition and the short-chain esterquat.

12. The method according to claim 11, wherein the at least one monocarboxylic acid comprises an acid corresponding to the general formula (I):

$$R^1CO\text{—}OH \quad (I)$$

wherein $R^1CO$ represents an acyl group having from 6 to 10 carbon atoms.

13. The method according to claim 12, wherein $R^1CO$ represents a linear, saturated acyl group having from 8 to 10 carbons atoms.

14. The method according to claim 11, wherein the at least one dicarboxylic acid comprises an acid corresponding to the general formula (II):

$$HOOC(CH_2)_nCOOH \quad (II)$$

wherein n represents a number of from 1 to 10.

15. The method according to claim 11, wherein the at least one dicarboxylic acid comprises adipic acid.

16. The method according to claim 13, wherein the at least one dicarboxylic acid comprises adipic acid.

17. The method according to claim 11, wherein the acyl groups derived from the at least one monocarboxylic acid and the acyl groups derived from the at least one dicarboxylic acid are present in a molar ratio of from 50:50 to 90:10.

18. The method according to claim 11, wherein the acyl groups derived from the at least one monocarboxylic acid and the acyl groups derived from the at least one dicarboxylic acid are present in a molar ratio of from 70:30 to 80:20.

19. The method according to claim 11, wherein the short-chain esterquat is combined with the composition in an amount of from 0.1 to 10% by weight, based on the composition.

20. The method according to claim 11, wherein the short-chain esterquat is combined with the composition in an amount of from 1 to 8% by weight, based on the composition.

* * * * *